United States Patent [19]
Tapper

[11] Patent Number: 6,094,594
[45] Date of Patent: *Jul. 25, 2000

[54] HAIR REMOVAL SYSTEM

[76] Inventor: Robert Tapper, 1935 Armacost Ave., Los Angeles, Calif. 90025

[ * ] Notice: This patent issued on a continued prosecution application filed under 37 CFR 1.53(d), and is subject to the twenty year patent term provisions of 35 U.S.C. 154(a)(2).

[21] Appl. No.: 08/696,721

[22] Filed: Aug. 14, 1996

[51] Int. Cl.$^7$ .................................................. A61N 1/30
[52] U.S. Cl. .............................. 604/20; 604/290; 8/161; 606/43; 606/131
[58] Field of Search ...................... 604/20, 290; 606/131, 606/133, 36, 43; 8/94.16, 161, 94.17

[56] References Cited

U.S. PATENT DOCUMENTS

| | | |
|---|---|---|
| 3,194,736 | 7/1965 | Braun et al. . |
| 4,121,904 | 10/1978 | Schamper ..................................... 8/161 |
| 4,325,367 | 4/1982 | Tapper . |
| 4,618,344 | 10/1986 | Wells ....................................... 8/94.16 |
| 5,215,520 | 6/1993 | Shroot et al. . |
| 5,224,927 | 7/1993 | Tapper ..................................... 604/20 |
| 5,669,916 | 9/1997 | Anderson . |

FOREIGN PATENT DOCUMENTS

| | | |
|---|---|---|
| 0 555 510 | 8/1993 | European Pat. Off. . |
| WO 94/17776 | 8/1994 | WIPO . |

OTHER PUBLICATIONS

Protopapa, Evangelia E. et al., "Effects of Proteolytic Enzymes Papain, Chymotrypsin and Trypsin on the Guinea Pig Skin", Rev. of Clin. Pham and Phamacokinetics, 8:2 (1994) pp. 84–88.

Woeber, Karlheinz, Physical Therapy in Skin Disorders, In: Handbuch de Haut– and Geschlechtskrankheiten, Suppl. vol. 5., Part 2.Ed.: Jadassohn, J. Berlin–Gottingen–Heidelberg, 14 pages.

Skin Reactions. I. Mechanism of Histamine Intophoresis From Aqueous Media, by Harold A. Abramson, M.D. & Armine Alley, Archives of Physical Therapy, X–Ray, Radium, Jun. 1937, pp. 327–332.

Transport Mechanisms in Iontophoresis by Pikal M.J., 1 page.

Increased Penetration of Nonelectrolytes in Mouse Skin During Iontophoretic Water Transport (Iontohydrokinesis) by Louis P. Gangarosa, No–Hee Par, Carold A Wiggins and James M. Hill, vol. 212, 1 page.

Five Effects Which Occur in the Tissues When the Galvanic Current is Applied by Clayton Williams, Medical Galvanism—Indications & Techniques, 2 pages.

Iontophoretic Delivery of Drugs: Fundamentals, Developments and Biomedical Applications by Ajay K. Banga and Yie W. Chien, 1 page.

Skin Permeability by H. Schaefer, A. Zesch & G. Stuttgen, Springer–Verlag, 1982, 2 pages.

Iontophoretic Transport of Nonelectrolytes, 1980, 1 page.

Iontophoretic Devices for Drug Delivery by Praveen Tyle, Pharmaceutical Research, vol. 3, Nov. 6, 1986, 1 page.

Depilatories by Richard H. Barry, Ph.D., Chapter 18, Cosmetics: Science and Technology, Basssam & Sagarin, pp. 39–72.

Chemical Removal of Hair by Allen J. Natow, MD, Cosmetology, Aug. 1986, pp. 91 & 92.

The Direct Current and Ion Transfer by Arthur L. Watkins, M.D., A Manual of Electrotherapy, 3rd Edition, 2 pages.

Removal of Hair by Electrophoresis of Lydasa in Saturated Solution of Sodium Chloride by T. Y. Gorshkova, Leningrad Cosmetic Clinic, 3 pages.

(List continued on next page.)

Primary Examiner—Mark Bockelman
Attorney, Agent, or Firm—Fulwider Patton Lee & Utecht, LLP

[57] ABSTRACT

A method and apparatus for selective long term and/or permanent hair removal from a biological subject by iontophoretic delivery of a chemical depilatory agent deeply into a hair removal site for effecting varying degrees of damage to hair roots.

16 Claims, 2 Drawing Sheets

OTHER PUBLICATIONS

Treatment by Ion Transfer (Iontophoresis) by D. Abramowitsch, M.D. and B. Neoussikine, M.D., 1946, 2 pages.

Hair Removal Techniques: Part Two by Zoe Diana Draelos, M.D., Cosmetic Dermatology, Nov. 1990, pp. 12–14.

Cream Depilatory, Organics Chemicals Div. of W. R. Grace & Co. Soap/Cosmetics/Chemical Specialties, Feb. 1991, 1 page.

Physical Metods for the Management of Hirsutism by Richard F. Wagner, Jr., M.D., Cutis, vol. 45, May 1990, p. 319.

HAIR REMOVAL SYSTEM

BACKGROUND OF THE INVENTION

This invention relates generally to improvements in methods and apparatus for hair removal and, more particularly, to a new and improved system capable of long term and/or permanent mass or individual hair removal from a biological subject by appropriate iontophoretic delivery of a depilatory agent.

It is common practice among most of the world's population to remove hair in order to improve personal appearance. The female is especially desirous of removing unwanted hair on the face, underarms, legs and other anatomical parts that may be exposed because of current fashions such as bikini bathing suits and the like. Besides genetic factors that lead to excess hair, modern medicine, notably steroids, also contribute to this cosmetic concern. The most popular means of hair removal is accomplished primarily by shaving with either a razor blade or electric shaver. Other means include tweezers, wax and depilatories. While these prior art methods have significant disadvantages such as cuts from razors, pain from tweezers and associated risk of infection, messiness of depilatories together with risk of irritation from such harsh chemicals, the common denominator that threads through this group is that such hair removal is usually only temporary. Therefore, such hair removal procedures must be repeated endlessly.

While depilatories have enjoyed relatively wide success as a temporary hair removal expedient, they have not proven successful where longer term or permanent hair removal is desired.

Currently, the most commonly used chemical depilatories are mercaptans, particularly salts of thioglycolic acid. The thioglycolates were patented in the 1930's for use in dehairing cattle hides. By the 1940's, cosmetically elegant alkaline creams containing thioglycolates were patented for human use, and they remain the standard chemical depilatories used today.

Thioglycolate depilatories work by hydrolyzing disulfide bonds. Hair strength is a function of the disulfide bonds between cystine molecules. Cystine forms 15 percent of the keratin in hair and 2 percent of the keratin in skin. This is why thioglycolates preferentially hydrolyze the keratin in hair over that in skin.

Modern formulations are usually aqueous solutions of thioglycolic acid mixed with alkali such as sodium hydroxide or calcium hydroxide. In addition to breaking disulfide bonds, these aqueous solutions of thioglycolates provide the important function of hydrating the hair shaft. This quickly gives the hair a jelly-like consistency so that it can be easily wiped away.

Thioglycolate depilatories are marketed as pastes, lotions, or creams. A thick layer is applied to the face so that the depilatory does not dry out and lose effectiveness. Depending on the formulation, the depilatory is left on for between two and fourteen minutes. After the preparation is removed, the hairs that remain are typically wiped away with a wash cloth. A moisturizer should also be applied afterward to suppress any irritation.

Depilatories are intended to act deep in the follicle where the hair shaft has not fully keratinized and therefore can rapidly absorb the chemical. As a result, several days usually elapse before the hair shaft is visible above the skin's surface. Also, for reasons that are not completely clear, the hair that regrows usually does not have the stubbly feel of shaven hair.

Although the thioglycolates are safe, adverse effects occur occasionally. Thioglycolate is a known contact allergen, and the fragrances used in depilatory preparations can also cause contact allergy. In addition, the alkalinity of certain preparations can cause an irritant dermatitis if left on the skin too long. Moreover, as previously indicated, hair removal is not permanent and hair regrowth is inevitable.

While thioglycolates are the most commonly used depilatories, they are not suitable for all situations. In particular, they are usually too slow in action to be useful to men with thick beards. Many men, especially blacks, suffer from pseudofolliculitis barbae ("razor bumps") in which the sharp tip of the shaven beard hair curls into the adjacent skin and causes a foreign body inflammatory reaction. Chemical depilation can help alleviate this problem by eliminating the possibility of nicking the "razor bumps" and by preventing stubbly, sharp-tipped hair from growing in. However, thioglycolates do not penetrate thick beard hairs rapidly enough to be a practical alternative to shaving. Instead, preparations based on strontium sulfide or barium sulfide must be used. These are more effective for removing thick beard hair within a reasonable period of time. However, sulfide depilatories are seriously limited by the foul odors released by hydrogen sulfide gas. This odor can be minimized by preventing water from coming in contact with the cream. However, even if nearly all of the cream is scraped off, some foul odor is almost always produced when the face is washed, and this has proven to be a significant deterrent to use of these products.

The only known permanent means for hair removal has been by way of electrolysis needle. This latter process is costly, painful, subject to scarification and extremely tedious since it treats only one hair at a time. Moreover, the electrolysis hair removal process often extends over a period of years.

While attempts have also been made to remove hair by iontophoresis and electroosmosis, such processes have not generally been as successful as desired and have been known to produce deleterious side effects.

Hence, those concerned with the development and use of hair removal systems and procedures have long recognized the need for improvements in hair removal methods and apparatus to enable more rapid, reliable, comfortable, convenient, economical, long term and/or permanent mass and/or individual removal of hair. As will become apparent from the ensuing discussion, the present invention fulfills all of these needs.

SUMMARY OF THE INVENTION

Briefly, and in general terms, the present invention provides a new and improved hair removal system for iontophoretically delivering a depilatory agent into a site where hair removal is desired.

Basically, the present invention is directed to methods and means for applying a suitable chemical depilatory agent to the site on a biological subject where hair is to be removed and subsequently iontophoretically delivering the depilatory agent deeply into the site to promote substantial damage or total destruction of the hair roots whereby long term and/or permanent hair removal is selectively accomplished.

In a presently preferred embodiment, by way of example and not necessarily by way of limitation, non-metallic iontophoresis electrodes and a chemical depilatory of preferably low viscosity are utilized for enhanced efficacy. The depilatory is preferably contained within felt storage pads or the like adjacent the electrodes of the iontophoretic delivery device. Alternatively, the depilatory agent may be topically applied directly to the hair at the site where hair removal is desired and iontophoresis is subsequently used to drive the depilatory into the site for controlled hair root destruction. In this latter case a depilatory of higher viscosity, spread over a larger surface area is preferred. The magnitude of the electrical current and the duration of treatment may be manipulated to effect varying degrees of hair root damage and thereby selectively accomplish either long term or permanent hair removal.

Hence, the new and improved hair removal methods and apparatus of the present invention enable more rapid, reliable, comfortable, convenient, economical, long term and/or permanent mass and/or individual hair removal.

These and other objects and advantages of the invention will become more readily apparent from the following more detailed description of the invention, when taken in conjunction with the accompanying drawings of illustrative embodiments.

DESCRIPTION OF THE PREFERRED EMBODIMENTS

Figure 1:
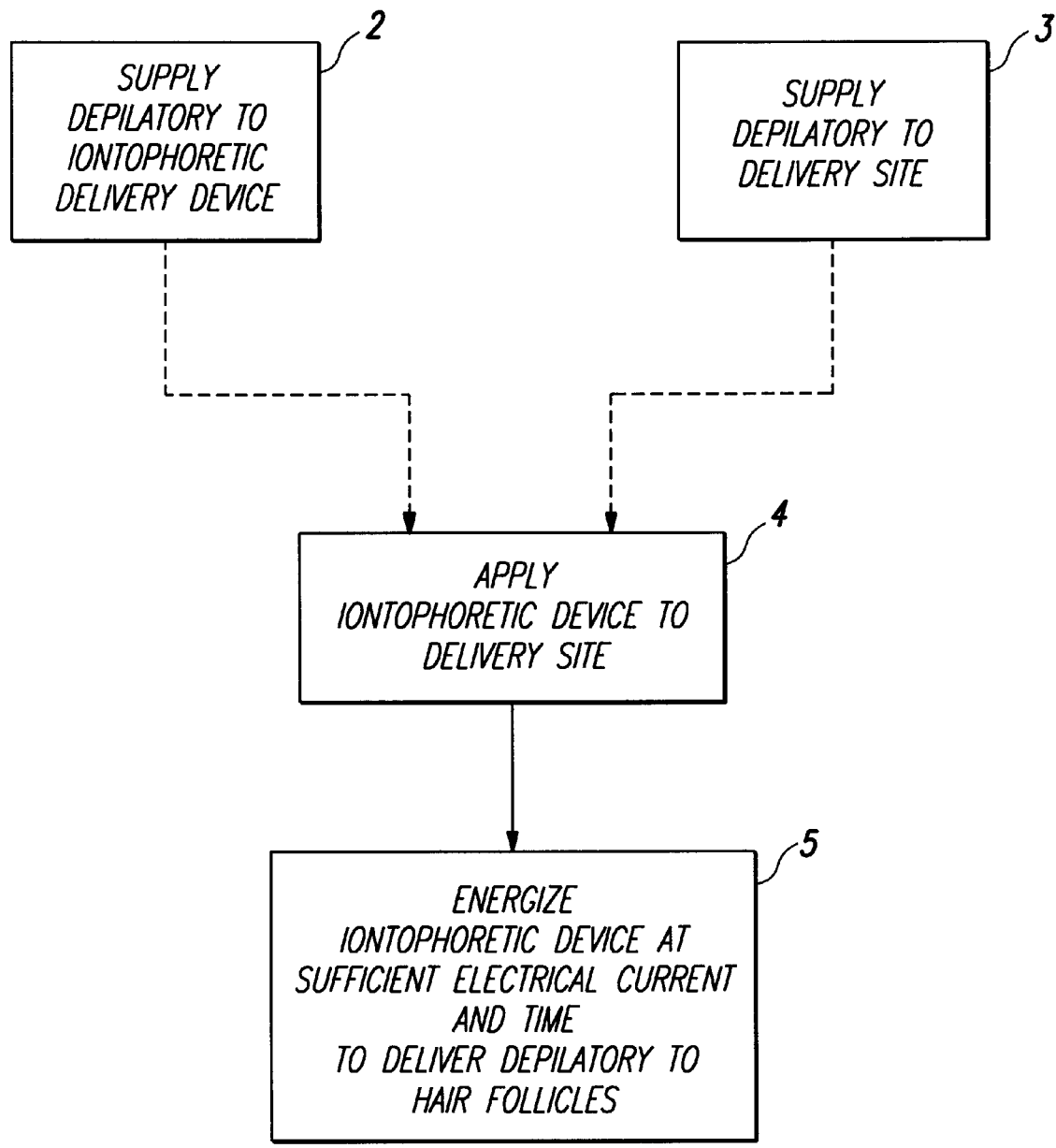
FIG. 1 is a flow chart illustrating a process embodying features of the present invention.

Referring now to the drawings, and more particularly to FIG. 1, there is shown a flow chart illustrating the basic processes practiced in various aspects of the present invention. In this regard, the purpose of the invention is to drive a suitable chemical depilatory agent deeply into a selected hair removal site located on a suitable biological subject, to effect varying degrees of damage to the hair roots for selective long term and/or permanent mass or individual hair removal at the selected site.

The most widely used depilatories are highly alkaline creams containing calcium thioglycolates. Hair is composed primarily of the chemical keratin. One of keratin's building blocks is the sulfur-containing amino acid cystine. Cystine makes up 15 to 17 percent of the hair. The alkali and the thioglycolate attack the cystine and break the linkages which hold the keratin molecules together. The hair absorbs water, swells, loses its strength, becomes almost like jelly, and can easily be scraped away from the skin. Because approximately eight times more keratin is found in the hair than in the skin, the depilatory cream will preferentially act more readily on hair than skin. Therefore, in a properly formulated product, the hair can usually be removed without substantially affecting the surrounding skin adversely. Of greatest significance, however, is that the hair removal is only temporary and does not prevent regrowth of hair.

In FIG. 1, in alternative steps 2 or 3, a depilatory agent, such as one including thioglycolate, and of relatively low viscosity, is either supplied to the storage pads of a suitable iontophoretic device (as in step 2) or applied topically to the hairs to be removed (as in step 3). In step 4, the iontophoretic device is then applied to the selected hair removal site where the depilatory is to be delivered and, in step 5, the iontophoretic device is electrically energized with sufficient magnitude of electrical current and for sufficient periods of time to effect the desired degree of hair root damage for either long term or permanent hair removal. If applied topically, the depilatory is preferably of high viscosity and spread over a larger surface area than that of the electrode applied to the skin.

The present invention accomplishes the ultimate hair removal process, a procedure that is at once either long term or permanent and involves multiple or massive hair removal. The process of electrolysis is well known for achieving permanency by introducing a needle into the follicle, having the needle connected to the negative terminal of a battery, with the body grounded remotely, and thus causing the collection of caustic sodium hydroxide to decompose the papilla and surrounding tissue. In developing the present invention, it was recognized that by introducing to the papilla the equivalent of the electrolysis chemical, i.e., a highly alkaline chemical, the same destructive events would take place resulting in substantial damage and either long term or permanent hair removal. Such a chemical is found in commonly used depilatories, the active ingredient being of the thioglycolate family or sodium sulfide with adjuvant chemicals present. In normal use, such depilatories are applied topically and so have no reliable means for effectively reaching the hair root system, i.e. the papilla, for permanent destruction. In accordance with the invention, an iontophoretic device is utilized to drive ions of the active chemicals of common depilatories to the root system of the growing hair and thus destroy or substantially impair the means for that hair to generate a new hair. In addition, the system can accomplish this over a wide area simultaneously to many hairs, limited only by the size of the iontophoretic applicator. The size is simply dictated by design.

One example of an iontophoretic delivery device particularly suitable for practice of the present invention is disclosed in U.S. Pat. No. 5,224,927 issued Jul. 6, 1993, entitled "Iontophoretic Treatment System", inventor Robert Tapper, and the disclosure of that patent is specifically incorporated herein by reference.

Figure 2:
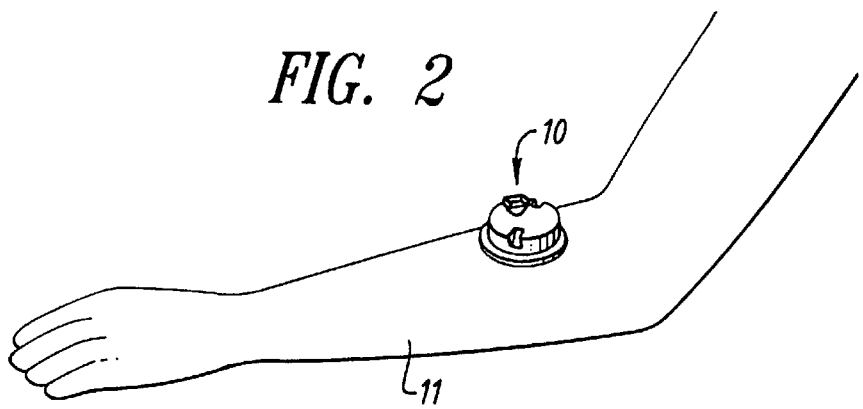
FIG. 2 illustrates an iontophoretic patch administration device suitable for use in the practice of the present invention, and shown installed upon the arm of a human subject.

As observed in FIG. 2, an iontophoretic patch administration device 10, of relatively simple economical, reliable and compact construction, and suitable for the practice of the present invention, is shown installed upon the arm 11 of a suitable biological subject so that the patch contacts the skin of the subject for appropriate administration of desired hair removal treatment by iontophoretic delivery of a suitable chemical depilatory or the like.

While the device 10 is shown in FIG. 2 as a compact patch, it will be appreciated by those of ordinary skill in the art that a larger structural and/or physical packaging unit (not shown) may be utilized, including a terminal electrode applicator for contact with the skin, and also embodying similar operational features.

Figure 3:
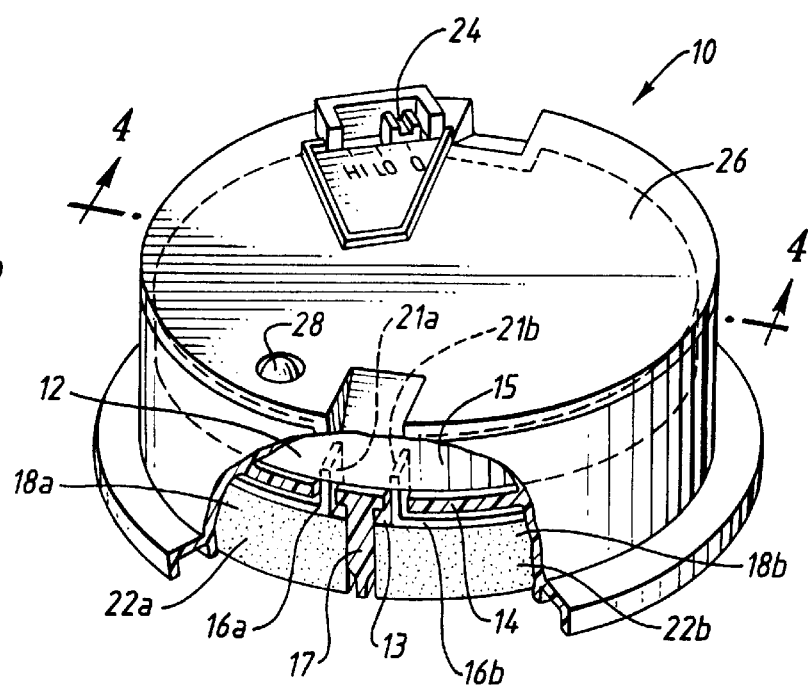
FIG. 3 is an enlarged, perspective view of the iontophoretic patch shown in FIG. 2, portions being broken away to illustrate internal structure.
Figure 4:
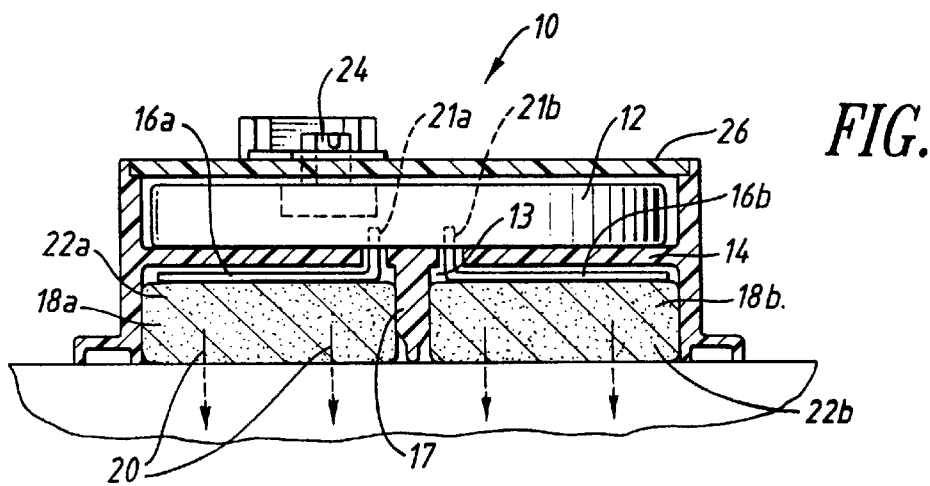
FIG. 4 is a sectional view, taken substantially along the line 4—4 in FIG. 3.

As best observed in FIGS. 3 and 4 of the drawings, the iontophoretic patch 10 is a very compact, circular, cylindrical device fabricated primarily of an outer plastic shell with internal, preferably integrally molded, baffles. The plastic shell and baffles are typically molded of an electrically insulating, flexible vinyl material or the like.

The internal baffles divide the interior of the iontophoretic patch 10 (currently marketed under the trademark LECTRO PATCH by General Medical Company of Los Angeles, Calif.) into upper and lower, hollow internal chambers 12 and 13, respectively, more specifically, by means of an interior baffle member 14. The upper chamber 12 contains a compact electronics package 15, including a suitable microchip and battery power supply. This upper chamber 12 is electrically insulated from the lower chamber 13 by the plastic baffle member 14.

The lower chamber 13 contains a pair of iontophoretic electrodes, 16a and 16b, typically of electrically conductive silicone/carbon material, and which are separated from each other by an electrically non-conductive plastic divider baffle 17 forming a separator wall which divides the lower compartment 13 into a pair of semi-circular electrode chambers and reservoirs 18a and 18b. The chambers 18a and 18b house the electrodes 16a, 16b and contain the appropriate substances such as a chemical depilatory agent to be ultimately administered to the biological subject at the selected hair removal site, the depilatory delivery path being indicated generally by the arrows 20 in FIG. 4.

The iontophoretic electrodes 16a, 16b are suitably connected electrically into the electronics package 15 via electrically conductive tabs 21a and 21b, respectively, extending through appropriate slotted openings in the chamber dividing baffle member 14. The silicone/carbon electrodes 16a, 16b are typically fabricated of 1–2 ohm per square centimeter conductive plastic material. While the electrodes 16a, 16b are preferably of silicone/carbon in a presently preferred embodiment of the invention, they may be fabricated of other electrically conductive, non-corrosive materials as well. Preferably, however, non-metallic electrodes are used where a chemical depilatory is to be delivered. With the AC signal used in this system, there is little or no resistance build-up in the silicone/carbon electrodes.

The drug reservoirs 18a and 18b typically contain a pair of felt pads 22a and 22b which have been appropriately saturated with the substances, i.e., a suitable chemical depilatory agent, to be dispensed.

In addition, an electrical slide switch 24, allowing selection of dosage and treatment duration, projects physically, for access by an operator, through an upper plastic cover plate 26 adhered to the top of the outer shell of the iontophoretic device 10. The switch 24 is electrically connected in the chamber 12 to the electronics package 15. The switch 24 may be selectively moved between a "0" (off) position, to either a "LO" (low current or lower rate of depilatory delivery) or "HI" (high current or higher rate of depilatory delivery) switch positions, to either turn the device 10 "off" so as to cease electrical operation, or to set the device for either high or low electric current rate operation.

An LED test indicator 28 extends from the electronics package chamber 12 below the cover plate 26, through an appropriate opening in the cover plate, and is observable from the top of the iontophoretic patch 10 to confirm proper electrical operation of the system for the user.

There are some unique features in the design of the iontophoretic patch 10 that enable it to excel in performing the job of permanent and/or long term mass hair removal compared to other iontophoretic designs. In this regard, features of the patch 10 that make it especially suitable to drive depilatories to the hair root are as follows:

1. The patch 10 uses conductive silicone carbon electrodes, while other iontophoretic devices typically use various metal electrodes. The thioglycolate depilatories are known to be sensitive to metals. When current flows through an iontophoretic applicator with metal electrodes, metallic ions are released that oxidize the thioglycolate and may substantially reduce its effectiveness. Moreover, metallic ions reaching the skin are known to precipitate skin proteins which hinder the flow of the desired chemical to the target site.

2. Since depilatories are formulated up to the highest tolerable pH for maximum effectiveness, e.g., typically 12.5, increasing the pH beyond this point risks skin damage. Conventional iontophoretic devices, being typically monopolar by design, would drive the depilatory into the skin and add to the pH level because they produce sodium hydroxide at the electrode which will combine with the alkaline depilatory and exceed safe biological levels. Since the patch 10 disclosed herein uses an AC signal, these deleterious electrode ions are neutralized and the depilatory pH does not exceed the maximum formulated value of approximately 12.5.

3. Where the depilatory is first soaked into the electrode pads, it is desirable to formulate the depilatory to be less viscous (for maximum performance) than the surface application types typically available over-the-counter although adequate performance can be obtained with over-the-counter formulations. In this regard, the depilatory used in iontophoresis is intended to soak the reservoir pad and the formulations available over-the-counter are generally of a high viscosity cream or lotion consistency. The latter is more suitable for topical application.

4. One means of introducing the depilatory to the pad is to presoak the pad 22a, 22b with the depilatory, let it dry and then allow the user to add water to reconstitute to a wet pad when ready to use. This can be done by adding water to an anhydrous depilatory (such as that disclosed in U.S. Pat. No. 3,194,736) for a "built-in" depilatory pad. Such pads would typically be replaceable. Alternatively, a cream or lotion depilatory may be used. However, it is more difficult to saturate the pads 22a, 22b with such viscous depilatories and it may be desirable in such instances to apply the depilatory directly to the electrodes.

5. Still another variation is the ability to accomplish either permanent hair removal or long term but temporary removal. The latter has significant appeal to the male population who may prefer not having to shave on a daily basis, but may desire a moustache appendage or the like at some future time. Moreover, the male may not be entirely happy with the totally "smooth" look of permanent hair removal and may prefer the vestiges of a male beard. To effect long term but temporary hair removal, the depilatory could be made less effective formula-wise for hair removal, or the iontophoretic delivery device could deliver lower electrical currents and/or be applied for shorter periods of treatment.

Of course, as previously indicated, the iontophoretic delivery device is not limited to being physically packaged as a patch 10. A larger electronics package may be housed in a remote instrument containing the electronics package, and either battery or plug-in electrical power may be utilized. A local applicator would then be electrically connected by cable to the remote instrument. The applicator would house suitable iontophoretic electrodes and drug reservoirs akin to the chamber 13 of the patch 10 in FIGS. 2–4.

Furthermore, while the process of the present invention has been described with respect to mass hair removal, it will be apparent that one of ordinary skill in the art may readily apply the same process for removal of individual hairs, without in any way departing from the spirit and scope of the invention. In this regard, for example, individual hairs may be wetted with a depilatory and typically a smaller, tailored electrode would be utilized to iontophoretically drive the depilatory into the hair follicle and destroy the papilla.

Although other chemical depilatory agents may be used in the practice of the invention, depilatories containing thioglycolates are preferred, as are compositions of low viscosity and a water-like consistency which are easily absorbed by the felt pads 22a and 22b, previously described. The higher viscosity depilatories are more useful in the embodiment of the invention where the depilatory is applied directly to the delivery site rather than to the electrode pads. All such depilatories should also preferably be mild enough to treat the facial area in addition to other areas of the body. Suitable depilatories commonly available are marketed under the brand names "NAIR" (manufactured by Carter-Wallace, Inc.) and "NEET" (manufactured by Whitehall Laboratories, Inc.). Such formulations, with the thickening ingredient removed to enhance absorption by the pads 22a and 22b, are preferable in the practice of the present invention where the electrode pads are soaked with the depilatory, but the thickening agent may be left intact if the depilatory is applied topically directly to the delivery site.

In addition to the active ingredients—calcium salt, thioglycolic acid, and calcium hydroxide or another alkali—depilatory creams usually contain several or all of the following: surfactants, to emulsify (suspend) any fats, oils and water used in preparation of the product and to promote wetting of the hair and washing off of the preparation; humectants (glycerol, propylene glycol), to prevent quick drying on the skin; water; polyethylene glycols; and fats, oils, or other fat materials.

Typically, hair removal is accomplished with iontophoresis currents that may vary from approximately 0.5 ma. to approximately 1.0 ma. and for durations of treatment between approximately a few minutes and approximately fifteen minutes. Of course, this is by way of example only and may vary widely to establish desired electrical current density (e.g. less than 0.5 ma per $cm^2$), depending upon the particular chemical depilatory used, the size (area) of the iontophoresis electrodes adjacent the hair removal site, the tolerable comfort threshold and the extent of hair removal desired, i.e., long term or permanent. Reasonable experimentation with these parameters will produce the desired results. Typically, lower currents and shorter time durations are used initially to mitigate skin irritation and to determine experimentally the effect upon the hair for the particular subject and particular part of the anatomy where hair removal is desired.

Hence, the new and improved hair removal methods and apparatus of the present invention satisfy a long existing need for more rapid, reliable, comfortable, convenient, economical, long term and/or permanent mass and/or individual hair removal.

Accordingly, it will be apparent from the foregoing that, while particular forms of the invention have been illustrated and described, various modifications can be made without departing from the spirit and scope of the invention. Therefore, it is not intended that the invention be limited, except as by the appended claims.

I claim:

1. In a hair removal system, the combination comprising:
   iontophoretic means for delivering a chemical depilatory agent into the skin of a living human subject at a site where hair to be removed is located; and
   a non-enzyme chemical depilatory agent suitable for delivery into the skin by said iontophoretic means whereby long term or permanent hair removal is facilitated without physical injury to the human subject.

2. A combination as set forth in claim 1, wherein said iontophoretic means includes electrode means fabricated of electrically conductive, non-metallic materials.

3. A combination as set forth in claim 2, wherein said electrode means are fabricated of electrically conductive silicone/carbon.

4. A combination as set forth in claim 1, wherein said iontophoretic means comprises:
   a pair of closely spaced, electrically conductive electrodes adapted to be located adjacent said site for hair removal; and
   means for alternating the direction of electrical current flow between said electrodes.

5. A combination as set forth in claim 4, and further including an absorbent pad adjacent each of said electrodes, said pad containing said depilatory agent.

6. A combination as set forth in any of claims 1–5 wherein said depilatory agent includes a thioglycolate.

7. A combination as set forth in any of claims 1–5, wherein said depilatory agent has a substantially low viscosity.

8. A combination as set forth in any of claims 1–5 wherein said depilatory agent has a substantially high viscosity.

9. A combination as set forth in any of claims 1–5, wherein said depilatory agent has a water-like consistency.

10. A combination as set forth in any of claims 1–5, wherein said depilatory agent is anhydrous.

11. A method for long term or permanent hair removal, comprising the steps of:
    locating the site of hair to be removed from a living human subject; and
    iontophoretically delivering a non-enzyme chemical depilatory agent into said site and sufficiently deep to substantially damage hair papilla, whereby long term hair removal is accomplished without physical injury to the human subject.

12. A method as recited in claim 11, further including the step of:
    varying the magnitude and duration of electrical current for iontophoretic delivery to control the degree of effective hair removal.

13. A method as recited either of claims 11 or 12, wherein said depilatory agent includes a thioglycolate.

14. A method as recited either of claims 11 or 12, wherein said depilatory agent has a low viscosity.

15. A method as recited either of claims 11 or 12, wherein said depilatory agent has a high viscosity.

16. A method as recited either of claims 11 or 12, wherein said depilatory agent has a water-like consistency.

* * * * *